United States Patent [19]

Wong et al.

[11] Patent Number: 4,528,290

[45] Date of Patent: Jul. 9, 1985

[54] STIMULATING DOPAMINE D-1 RECEPTORS

[75] Inventors: David T. Wong; Mark M. Foreman, both of Indianapolis, Ind.

[73] Assignee: Eli Lilly and Company, Indianapolis, Ind.

[21] Appl. No.: 575,126

[22] Filed: Jan. 30, 1984

[51] Int. Cl.³ .................... A61K 31/47; A61K 31/495
[52] U.S. Cl. ..................................... 514/293; 514/267
[58] Field of Search ................................ 424/250, 258

[56] References Cited

U.S. PATENT DOCUMENTS 3,393,192  7/1968  Walter et al. ........................ 260/239
4,198,415  4/1980  Kornfeld et al. .................... 424/258
4,468,401  8/1984  Hahn .................................... 424/258

OTHER PUBLICATIONS

Poggioli et al., Rev di Farm. & Terop, 9213, (1978).
Ahlenius et al., J. Neural Transmission, 54–165, (1982).
Hyyppa et al., Acta Neurologia Scand. 46, Supp. 43, p. 223, (1970).
Pierini et al., Int. J. Fertil., 24–214, (1979).
Hahn et al., J.P.E.T., 224, 206 (1983), (Hahn II).
Titus et al., J. Med. Chem., 26, 1112, (1983).
Iorio et al., J.P.E.T., 226, 462, (1983).
Hyttel, Euro. J. Pharm., 91, 153, (1983).
Hahn & Wardell, J. Cardiovascular Pharm., 2, 583, (1980).
Pendleton et al., Euro. J. Pharm., 51, 19, (1978).
Hahn et al., J.P.E.T., 223, 305, (1982).
Weinstock et al., J. Med. Chem., 23, 973, (1980).
Stoof et al., Nature, 294, 366, (1981).
Stoof and Kebabian, Brain Res., 250, 263, (1982).
Memo et al., Science, 221, 1304, (1983).

Primary Examiner—Stanley J. Friedman
Attorney, Agent, or Firm—James L. Rowe; Arthur R. Whale

[57] ABSTRACT

Dopamine D-1 agonists, trans-(+)tautomers of the formula

3 Claims, No Drawings

STIMULATING DOPAMINE D-1 RECEPTORS

BACKGROUND OF THE INVENTION

The concept that various body tissues contain two dopamine receptors has only recently received general acceptance. These receptors have been designated as the D-1 and D-2 receptors. Several D-2 dopamine receptor agonists are known, including lergotrile and pergolide, both ergolines, and LY141865 (U.S. Pat. No. 4,148,415) an ergoline partial structure. These D-2 agonists have been found useful in treating Parkinson's disease as well as conditions in which there is an excess of circulating prolactin such as galactorrhea. LY141865 (trans-dl-5-n-propyl-4,4a,5,6,7,8,8a,9-octahydro-1H(and 2H)-pyrazolo[3,4-g]quinoline) has also been found to reduce blood pressure in mammals without the occurrence of postural hypertension. This antihypertensive activity is stated to be present in only one of the stereoisomers of the trans-(dl) racemate, the trans-(−)isomer, also named as 4aR,8aaR-5-n-propyl-4,4a,5,6,7,8,8a,9-octahydro-1H(and 2H)-pyrazolo[3,4-g]quinoline-see the copending application of Richard A. Hahn, Ser. No. 438,833, filed 11-3-82 now U.S. Pat. No. 4,468,401, issued 9-11-84. The same stereoisomer, as well as its parent racemate, has been found to be useful in treating sexual dysfunction in mammals—see the copending application of Mark M. Foreman, Ser. No. 518,906, filed 8-1-83, now abandoned, continuation-in-part application Ser. No. 636,959, filed 8-2-84.

Only a few drugs that affect the dopamine D-1 receptors are known. The first selective D-1 antagonist to be found was SCH-23390, R-(+)-7-hydroxy-8-chloro-2,3,4,5-tetrahydro-3-methyl-5-phenyl-1M-3-benzazepine—see Hyttel-*Euro. J. Pharm.*, 91, 153 (1983) and, Iorio et al, *J.P.E.T.*, 226, 462 (1983); see also U.S. Pat. No. 3,393,192 wherein the compounds are alleged to be anti-depressants, anti-bacterials, analgesics, and hypotensives.

SKF-38393, 1,2,3,4-tetrahydro-7,8-dihydroxy-1-phenyl-1H-3-benzazepine, is claimed to be a dopamine D-1 agonist. Hahn and Wardell, *J. Cardio-vascular. Pharm.*, 2, 583 (1980) describe the compound's activity as a renal vasodilator—see also Pendleton et al, *Euro. J. Pharm.*, 51, 16 (1978). SKF-82526, 6-chloro-7,8-dihydroxy-1-(4-hydroxyphenyl)-2,3,4,5-tetrahydro-(1H)-3-benzazepine has similar but improved properties—see Hahn et al, *J.P.E.T.*, 223, 305 (1982), and Weinstock et al, *J. Med. Chem.*, 23, 973 (1980). The compound is said to be a peripheral D-1 agonist without significant effect on central dopamine receptors, and is potentially useful in reversing the increased renal vascular resistance seen in many hypertensive patients.

Dopamine D-1 receptors, when stimulated by a D-1 agonist, are characterized by an increased cyclic AMP efflux. This effect is inhibited by D-2 agonists. Stoof and Kebabian discuss these D-1 agonist effects in papers appearing in *Nature*, 294, 266 (1981) and *Brian Res.*, 250, 263 (1982). An in vitro effect of D-1 agonists in the nuclei accumbens and caudatus tissue of schizophrenics is an increase in the activation of adenylate cyclase.

Nothing in the cited prior art would indicate that the trans (+) enantiomorph of a trans (−) selective D-2 agonist would have any independant activity, much less any D-1 agonist activity.

SUMMARY OF THE INVENTION

This invention provides a method for stimulating dopamine D-1 receptors in a mammal which comprises administering to said mammal a dopamine D-1 receptor stimulating amount of a trans-(+) stereoisomer existing as a tautomeric pair of the formula

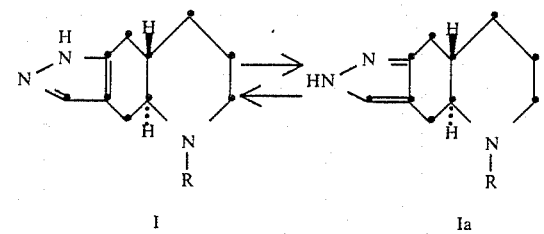

wherein R is methyl, ethyl, n-propyl or allyl.

Another group of extremely useful drugs are those represented by I and Ia in which R is n-propyl. The racemates, of which the tautomeric pair I and Ia is one component, are prepared by the procedure of Bach and Kornfeld, U.S. Pat. No. 4,198,415. Resolution of these racemates to yield the D-2 agonist, the trans-(−) or trans-4aR stereoisomer, is described in the copending application of Titus and Kornfeld, Ser. No. 439,238 filed 11-3-82. The trans-(+) or trans-4aS or 4aS,8aS stereoisomers useful in our novel physiological processes can be isolated from both the mother liquors and washes obtained during the above resolution procedure, which washes and mother liquors are enriched with regard to the trans-(+)isomer. The stereoisomeric resolving agent, (+)-tartaric acid, the opposite enantiomer from that employed in a resolution to obtain the trans-4aR stereoisomer, is particularly useful in obtaining the optically-pure trans-4aS isomer when added to the above referred to filtrates or washes. Alternatively, the intermediate trans(±)-1-substituted-6-oxodecahydroquinoline, available either from U.S. Pat. No. 4,198,415 or from the copending application of Schaus, Ser. No. 521,863, filed 8-10-83, can be resolved to yield the 4aS,-8aS-isomer by the method disclosed in the copending application of Schaus and Booher, Ser. No. 439,107, filed 11-3-82. This intermediate, optically-active trans-(+)-1-substituted-6-oxodecahydroquinoline can be transformed to the tautomeric pair I⇌Ia by the method of U.S. Pat. No. 4,198,415 or by the procedure disclosed in the copending application of Schaus, Ser. No. 438,834, filed 11-3-82.

Illustrative preparations of trans-(+)-stereoisomers useful in the processes of this invention are illustrated below in a series of examples.

EXAMPLE 1

Preparation of 4aS,8aS-5-n-propyl-4,4a,5,6,7,8,8a,9-octahydro-1H(and 2H)-pyrazolo[3,4-g]quinoline Ten grams of trans-(±)-5-n-propyl-4,4a,5,6,7,8,8a,9-octahydro-1H(and 2H)-pyrazolo[3,4-g]quinoline dihydrochloride were dissolved in water and the aqueous solution made basic by the addition of solid potassium carbonate. The aqueous phase was extracted several times with chloroform to remove the free base which had separated, being insoluble in the alkaline layer. The extracts were combined, the combined extracts dried and the solvent evaporated therefrom in vacuo. Four and seven tenths grams of a clear orange oil comprising trans-(±)-5-n-propyl-4,4a,5,6,7,8,8a,9-octahydro-1H(and 2H)-pyrazolo[3,4-g]-quinoline free base formed in the above neutralization were recovered. 1.8 g. of the free base were dissolved in methanol to which solution was added a hot solution of 1.5 g. of (+)-tartaric acid in methanol. The solution was heated to boiling for five minutes and was then allowed to cool to ambient temperature. A colorless crystalline solid enriched in the (+)-tartarate salt of 4aS,8aS-5-n-propyl-4,4a,5,6,7,8,8a,9-octahydro-1H(and 2H)-pyrazolo[3,4-g]quinoline precipitated. The precipitate was collected by filtration and the filter cake washed with ether to give 1.46 g. of solid. This fraction showed a rotation of $[\alpha]_D^{25}$(-H$_2$O)= +32.76° and melted at 173°–177° C. The solid ws recrystallized from hot methanol to give 0.70 g. of a colorless, crystalline solid which showed a rotation of $[\alpha]_D^{25}$(H$_2$O)= +58.44° and melted at 185°–186° C. This solid was recrystallized from hot methanol to give 0.15 gm. of the pure (+)-tartarate salt of 4aS,8aS-5-n-propyl-4,4a,5,6,7,8,8a,9-octahydro-1H(and 2H)-pyrazolo[3,4-g]quinoline as a colorless, crystalline solid with a rotation of $[\alpha]_D^{25}$(H$_2$O)= +93.88° and a melting point of 201°–202° C. Further recrystallization did not improve the melting point or optical rotation.

Calculated for C$_{17}$H$_{27}$N$_3$O$_6$: C, 55.27; H, 7.37; N, 11.37; Found: C, 55.00; H, 7.13; N, 11.19.

A resolution of trans-(±)-1-n-propyl-6-oxodecahydroquinoline was carried out according to the following procedure: Ten grams of (−)-di-p-toluoyltartaric acid were dissolved in 75 ml. of warm methanol. The solution was added to a solution of 5.05 g. of trans-[±]-1-n propyl-6-oxodecahydroquinoline in 15 ml. of methanol. The reaction mixture was brought to a boil and was then allowed to cool to ambient temperature. After remaining at ambient temperature overnight, crystallization was induced by the addition of seed crystals previously obtained. The crystallization tartarate was isolated by filtration and the filter cake washed with methanol. Yield=2.813 g. (18.7%) of a white crystalline solid comprising the (−)-di-p-toluoyltartrate of 4aR,8aR-1-n-propyl-6-oxodecahydroquinoline; $[\alpha]_D^{25°}$ = − 107.49° (MeOH, c = 1).

Filtrates and mother liquors from the above procedure or from similar, larger scale procedures, were combined to yield a solution of 1-n-propyl-6-oxodecahydroquinoline enriched as regards the 4aS,8aS-isomer, and depleted as regards the 4aR,8aR isomer. The solution was treated with (+)-ditoluoyl tartaric acid monohydrate, in accordance with the above procedure, to yield 4aS,8aS-1-n-propyl-6-oxodecahydroisoquinoline-(+)ditoluoyl tartrate of about 80% ee optical purity (ee=enantiomeric excess). 20 g. of the salt were crystallized from 250 ml. of methanol to give 12 g. of a white crystalline powder melting at 167.5°–169.5° C. with decomposition; $[\alpha]_D^{25}$ = +106.3° (methanol, c = 1.0); $[\alpha]_{365}^{25}$ = +506.7° (methanol, c = 1.0). These figures indicate an optical purity of about 90% ee. A second crop obtained from mother liquors from the above crystallization gave 2.3 g. of a white solid melting at about 166.0°–166.5° C. with decomposition; $[\alpha]_D^{25}$ = 106.6°; $[\alpha]_{365}^{25}$ = +510.8° (methanol, c = 1.0 for both) indicating optical purity of about 94% ee. Recrystallization of first and second crop crystals from methanol gave a white solid from which the free base was obtained by standard procedures. The free base was distilled to yield 4.14 g. of a colorless oil boiling at 82°–86° C. at 0.13 torr., comprising 4aS,8aS-1-n-propyl-6-oxodecahydroquinoline; $[\alpha]_D^{25}$ = +86.2°; $[\alpha]_{365}^{25}$ = +376.6° (methanol, c=1.0 for both rotations); optical purity = about 98% ee.

Next, 4.04 g. of the above free base were dissolved in 10 ml. of methanol to which was added a solution of 8.35 g. of (+)-ditoluoyl tartaric acid monohydrate in 65 ml. of methanol. The solution was concentrated to 50 ml. at which point a precipitate began to form. The solution was allowed to remain at ambient temperature overnight during which time further crystallization took place. The crystals were collected by filtration to give 10.87 g. of a white powder melting at 167.0°–167.5° C. The salt was converted to the free base which distilled at 82°–86° C. at 0.13 torr.; $[\alpha]_D^{25}$ = 86.9°; $[\alpha]_{365}^{25}$ = 378.8° (methanol, c = 1.0 for both) indicating an optical purity of about 98% ee.

Alternatively, trans-(±)-1-n-propyl-6-oxodecahydroquinoline can be treated directly with (+)-di-p-toluoyltartaric acid to yield the 4aS,8aS-1-n-propyl-6-oxodecahydroquinoline-(+)-di-p-toluoyl tartrate which is purified as set forth above for the 4aR,8aR salt.

4aS,8aS-1-n-propyl-6-oxodecahydroquinoline prepared as above was converted to 4aS,8aS-5-n-propyl-3,4,4a,5,6,7,8,8a,9-octahydro-1H(and 2H)-pyrazolo[4,5-g]-quinoline by the following procedure. Seven and seven tenths grams of potassium tertiary-butylate were dissolved in 85 ml. of THF and the resulting solution cooled to about 0° C. A mixture of 6.7 g. of 4aS,8aS-1-n-propyl-6-oxodecahydroquinoline and 10.2 g. of ethyl formate in 40 ml. of THF were added thereto. During the addition, gas was evolved. The reaction mixture was then allowed to warm to room temperature. TLC showed no starting material present. Six ml. of hydrazine hydrate were next added followed by sufficient 10% aqueous hydrochloric acid to bring the pH to about 9. The mixture was stirred vigorously at ambient temperature until tlc showed no formylketone intermediate was present. The reaction mixture was then poured into dilute aqueous sodium hydroxide solution and the alkaline mixture extracted with methylene dichloride. The methylene dichloride extract was dried and the solvent removed in vacuo to yield 9 g. of aa colorless foam. The foam was dissolved in 100 ml. of methanol to which was added an equivalent amount of 1M aqueous hydrochloric acid. The resulting solution was concentrated to yield a white solid which was recrystallized from a methanol/ethyl acetate solvent mixture. Five and sixty-eight hundredths grams of 4aS,8aS-5-n-propyl-4,4a,5,6,7,8,8a,9-octahydro-1H(and 2H)-pyrazolo[3,4-g]quinoline hydrochloride were obtained.

Other 4aS,8aS-5-substituted-octahydro-1H(and 2H)-pyrazolo[3,4-g]quinolines formulas I and Ia above can be prepared from the corresponding racemates in similar fashion by similar procedures using the same or similar resolving agents.

The above processes yield salts. Conversion of the salt thus obtained to the corresponding free base is readily effected by dissolving the salt in water and then adding an excess of an aqueous base (NaOH, Na$_2$CO$_3$ etc.). The free base, being insoluble in the basic solution, separates and is extracted with a water-immiscible organic solvent. The organic extract is then separated and dried. A solution containing one equivalent of a different non-toxic acid is then added, and the resulting salt isolated by filtration or by evaporation of the solvent. Alternatively, the solvent can be removed from the dried organic extract and the free base obtained as a residue. The free base can then be dissolved in a suitable solvent and the non-toxic acid added as a solution. The preferred salt for use in the novel processes and formulations of this invention is the HCl salt which can be prepared, for example, by adding an equivalent of ethanolic hydrogen chloride to an ethanolic solution of the free base, followed by evaporation of the ethanol and recrystallization of the salt. If it is desired to make a di salt such as a dihydrochloride salt, HCl gas can be passed into a solution of the free base to the point of saturation and the di salt isolated by filtration.

Compounds represented by the tautomeric pair I⇌Ia above each have two or more basic centers. The most basic of these is the octahydroquinoline ring amino group. This group forms salts readily with pharmaceutically-acceptable acids. Amine groups of lesser basicity are also present in I and Ia and these groups will form salts with strong pharmaceutically-acceptable inorganic acids, such as the mineral acids, or strong organic acids such as p-toluenesulfonic acid, to yield di salts. Pharmaceutically-acceptable acid addition salts of the compounds represented by I and Ia above thus include mono or di salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxyalkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Representative compounds useful in our novel physiological processes thus include:
4aS,8aS-5-methyl-4,4a,5,6,7,8,8a,9-octahydro-1H(and 2H)-pyrazolo[3,4-g]quinoline tartrate,
4aS,8aS-5-ethyl-4,4a,5,6,7,8,8a,9-octahydro-1H(and 2H)-pyrazolo[3,4-g]quinoline dihydrochloride,
4aS,8aS-5-n-propyl-4,4a,5,6,7,8,8a,9-octahydro-1H(and 2H)-pyrazolo[3,4-g]quinoline dihydrochloride, and the like.

In carrying out our novel therapeutic processes, compounds according to I"Ia above are administered in the form of a salt formed with a non-toxic acid to mammals in need of treatment by either the oral or parenteral route at a dose level sufficient to stimulate D-1 receptors, said dose level varying from 0.01-15 mg./kg./day.

For parenteral administration, a water soluble salt of, for example, 4aS,8aS-5-n-propyl-4,4a,5,6,7,8,8a,9-octahydro-2H(and 1H)-pyrazolo[3,4-g]quinoline, is dissolved in an isotonic salt solution and administered by that route. For oral administration, a pharmaceutically-acceptable salt of the drug is mixed with standard pharmaceutical excipients such as starch and loaded into capsules, each containing 0.1-15 mg. of active drug. The oral dosage would be administered 3-4 times per day, giving a daily dosage range of about 0.3 to about 60 mg./kg. per day.

Other oral dosage forms such as suspensions, elixers and tablets, can also be utilized and are preparable by standard procedures.

The following illustrates specific oral dosage forms:
A tablet formulation is prepared using the ingredients below:

|  | Quantity (mg./tablet) |
| --- | --- |
| Active compound | .1-15 |
| Cellulose, microcrystalline | 400 |
| Silicon dioxide, fumed | 10 |
| Stearic acid | 5 |

The components are blended and compressed to form tablets.

Alternatively, tablets each containing 0.1-15 mg. of active ingredient are made up as follows:

| Active ingredient | .1-15 mg. |
| --- | --- |
| Starch | 45 mg. |
| Microcrystalline cellulose | 35 mg. |
| Polyvinylpyrrolidone | 4 mg. |
| (as 10% solution in water) | |
| Sodium carboxymethyl starch | 4.5 mg. |
| Magnesium stearate | 0.5 mg. |
| Talc | 1 mg. |

Telescoping gelatin capsules each containing 0.1-15 mg. of medicament have the following composition.
Active ingredient: 0.1-15 mg.
Starch: 59 mg.
Microcrystalline cellulose: 59 mg.
Magnesium stearage: 2 mg.

To prepare such capsules, the active ingredient, cellulose, starch and magnesium stearate are blended, passed through a No. 45 mesh U.S. sieve, and filled into hard telescoping gelatin capsules.

Suspensions each containing 0.1-15 mg. of medicament per 5 ml. dose are made as follows:
Active ingredient: 0.1-15 mg.
Sodium carboxymethyl cellulose: 50 mg.
Syrup: 1.25 ml.
Benzoic acid solution: 0.10 ml.
Flavor: q.v.
Color: q.v.
Purified water to: 5 ml.

The medicament is passed through a No. 45 mesh U.S. sieve and mixed with the sodium carboxymethylcellulose and syrup to form a smooth paste. The benzoic acid solution, flavor and color are diluted with some of the water and added with stirring. Sufficient water is then added to produce the required volume.

Compounds represented by the above formulas manifest their dopamine D-1 agonist activity in several ways. For example, 4aS,8aS-5-n-propyl-4,4a,5,6,7,8,8a,9-octahydro-1H(and 2H)-pyrazolo[4,3-g]quinoline stimulated cyclic AMP formation in rat striatal membrane.

In this determination, the procedure of Wong and Reid, *Communications in Psychoparmacology*, 4, 269 (1980) was employed. 4aS,8aS-5-n-propyl-4,4a,5,6,7,8,,8a,9-octahydro-1H(and 2H)-pyrazolo[4,3-quinoline, the 4aR,8aR enantiomer and the corresponding racemate were tested for their ability to activate adenylate cyclase in rat striatal membrane as measured by an increase in cyclic AMP concentration. The results of this determination are given in Table 1. Dopamine was used as a positive control. In the table, column 1 gives the drug used, column 2, drug concentration, and column 3, cyclic AMP formation as percent of control.

TABLE 1

| Drug | Conc. in micromoles | Cyclic AMP Formation as a percent of control |
| --- | --- | --- |
| Dopamine | 10 | 149.7 ± 7.2* |
|  | 50 | 215.5 ± 28.8* |
|  | 100 | 183.8 ± 12.5* |
| Racemate | 50 | 116.5 ± 13.3 |
| 4aR, 8aR enantiomer | 50 | 114.2 ± 10.4 |
| 4aS, 8aS enantiomer | 50 | 141.8 ± 9.3* |

In the presence of 10 micromolar GTP, the basal adenylate cyclase activity in rat striatal membranes has a mean ±S.E. value of 134.9±6.1 pmole/min/mg of protein. Compounds were examined in three or more separate experiments. Significant increases ($p<0.025$) in cyclic AMP formation are identified with asterisks.

According to the information presented in Table 1, only the 4aS,8aS enantiomer significantly increased cyclic AMP formation, indicating D-1 dopamine agonist activity.

A second, particularly sensitive indicator of D-1 agonist activity is the determination of the cyclic AMP efflux in tissue slices using a procedure based on Stoof and Kebabian (loc. cit). In this procedure, striatal tissue is dissected from rat brains and chopped into 0.3 mm.×0.03 mm. fragments. The tissue fragments are suspended in the appropriate buffer system (Earl's balanced salt solution, for example) and the suspension is continuously aerated with 95:5 $O_2/CO_2$ while being maintained at 37° C. Just prior to use, the tissue fragments are transferred to fresh media to which is added bovine serum albumin (2.5 mg./ml.) and 3-isobutyl-1-methylxanthine (1 millimolar) to block degradation of cyclic AMP. The tissue fragments are incubated in buffer without drugs and are then transferred to the same media with added drug. Aliquots of incubation media, with and without drugs, are assayed for cyclic AMP concentration by a specific radioimmunoassay. The effect of the drug or drugs on efflux is expressed as a percentage of the resting efflux. The following medium was employed:

| Medium Ingredient | Conc. Mg./Liter |
| --- | --- |
| NaCl | 4800 |
| KCl | 402.6 |
| $NaHCO_3$ | 2201.1 |
| $NaH_2PO_4$ | 137.99 |
| $MgSO_4.7H_2O$ | 147.88 |
| d-glucose | 1009 |
| $CaCl_2.2H_2O$ | 191.1 |
| phenol red | 10 |

In the experiments described in the abovementioned reference, Stoof and Kebabian employed sulpiride to repress the negative (anti D-1) effect of any drug acting as a dopamine D-2 agonist. The authors had previously demonstrated that a D-2 agonist repressed cyclic AMP formation (an opposite effect from that produced by a D-1 agonist). Sulpiride is known to be an antagonist on pituitary D-2 receptors. Addition of sulpiride to a test system, such as that described above, blocks any D-2 effect of a drug in reducing cyclic AMP production. Stoof and Kebabian were able to demonstrate a lack of effect of sulpiride on cyclic AMP production in striatal tissue using SKF 38393 as a pure D-1 agonist, an indication that D-2 receptors were not involved and the compound did not have D-2 agonist activity.

The results of one such determination for 4aS,8aS-5-n-propyl-4,4a,5,6,7,8,8a,9-octahydro-1H(and 2H)-pyrazolo[3,4-g]quinoline dihydrochloride (compound A), are given in Table 2. In the table, column 1 gives the added drug, if any; column 2, the drug concentration; column 3, the level of cyclic AMP present; and column 4, the percent increase in cyclic AMP concentration.

TABLE 2

| Drug | Concentration | Cyclic AMP Concentration | % Increase in Cyclic AMP |
| --- | --- | --- | --- |
| None |  | 71.6 ± 8.2 | 0 |
| A | $5 \times 10^{-7}$ M | 131.0 ± 9.2 | 83 |
| A | $5 \times 10^{-6}$ M | 160.1 ± 23.8 | 124 |
| A plus sulpiride at $10^{-6}$ M | $5 \times 10^{-7}$ M | 143.7 ± 6.2 | 100 |

In the above table, it is noted that sulpiride had no effect on the increase in cyclic AMP efflux.

In previous work by Stoof and Kebabian, the racemate, trans-(±)-5-n-propyl-4,4a,5,6,7,8,8a,9-octahydro-1H(and 2H)-pyrazolo[4,3-g]quinoline (LY141865), was found to lower cyclic AMP levels (see chart G page 367 of Stoof and Kebabian). Addition of sulpiride had little or no effect and, at best, restored the cyclic AMP levels to control levels. The same racemic drug reduced the effect of SKF38393 in increasing cyclic AMP levels by 57±8% (FIG. 3 page 368 of Stoof and Kebabian). Addition of sulpiride suppressed this effect and cyclic AMP levels were substantially the same as those found with SKF38393 alone.

The data presented by Stoof and Kebabian are consistent with the conclusion that the 4aR,8aR-enantiomer, a known D-2 agonist, is the active component of the racemate, LY141865, in suppressing cyclic AMP formation, which effect is in turn suppressed by sulpiride. The trans-(+)-isomer was without D-2 agonist activity in tests for D-2 agonist activity.

In a separate, but similar, experiment, the fact that SKF38393 increases cyclic AMP production was verified (145% at a $10^{-6}$ molar concentration). This effect was lowered by the addition of 4aR,8aR-5-n-propyl-4,4a,5,6,7,8,8a,9-octahydro-1H(and 2H)-pyrazolo[4,3-g]-quinoline, the trans-(−)-enantiomer and a D-2 agonist, at $0.5 \times 10^{-6}$M (145% down to 42%). This effect was suppressed by the addition of sulpiride ($10^{-6}$M) to the system.

We claim:

1. A method for stimulating dopamine D-1 receptors which comprises administering to a mammal a dopamine D-1 receptor stimulating amount of a trans-(+) stereoisomer existing as a tautomeric part of the formula

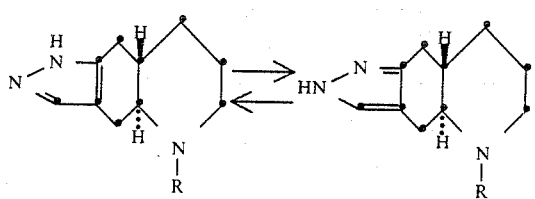
wherein R is methyl, ethyl, n-propyl or allyl.
2. A process according to claim 1 in which, in the drug used, R is n-propyl.
3. A process according to claim 1 in which 4aS,8aS-5-n-propyl-4,4a,5,6,7,8,8a,9-octahydro-1H(and 2H)-pyrazolo[3,4-g]quinoline or a pharmaceutically-acceptable acid solution salt thereof is the D-1 agonist employed.
* * * * *